United States Patent [19]

Bell et al.

[11] Patent Number: 4,920,128
[45] Date of Patent: Apr. 24, 1990

[54] PYRAZOLO[3,4-B]QUINOLINES AND THEIR USE AS ANTIVIRAL AGENTS

[75] Inventors: Malcolm R. Bell, East Greenbush; James H. Ackerman, Albany, both of N.Y.

[73] Assignee: Sterling Drug Inc., New York, N.Y.

[21] Appl. No.: 196,598

[22] Filed: May 20, 1988

Related U.S. Application Data

[63] Continuation-in-part of Ser. No. 71,110, Jul. 8, 1987, abandoned.

[51] Int. Cl.$^5$ ............... A61K 31/415; A61K 31/435; C07D 413/00; C07D 471/00
[52] U.S. Cl. ................... 514/293; 514/232.8; 514/934; 544/126; 546/82
[58] Field of Search ................... 546/82; 544/126; 514/232.8, 293, 934

[56] References Cited

PUBLICATIONS

Chem. Abstracts, Radl et al., vol. 106; 18429p, No. 106; 845446y (1987).
Chem. Abstracts, Radl et al., vol. 105; 226434t, No. 25 (1986).
Chem. Abstracts, Radl et al., vol. 104, No. 13; 109528v (1986).
Yoshida et al., Yakugaku Zasshi, 96, 33–6 (1976); Chemical Abstracts, 84: 121754s.
Holla et al., Bull. Chem. Soc. Japan, 57, 2984–6 (1984).
Neelima et al., J. Heterocyclic Chem., 23, 925–928 (1986).

*Primary Examiner*—Mary C. Lee
*Assistant Examiner*—J. Richter
*Attorney, Agent, or Firm*—Thomas L. Johnson; Paul E. Dupont

[57] ABSTRACT

Pyrazolo[3,4-b]quinolines having the formula

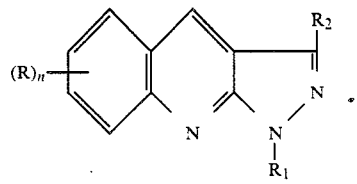

where R is hydrogen, hydroxy or alkoxy; $R_2$ is halogen, cyano, carbamyl, carboxy, lower-alkylcarbonyl, amino or aminomethyl; and $R_1$ is hydrogen or selected substituents as defined herein, are useful as antiviral agents and/or as vasodilators.

12 Claims, No Drawings

PYRAZOLO[3,4-B]QUINOLINES AND THEIR USE AS ANTIVIRAL AGENTS

This application is a continuation-in-part of application Ser. No. 71,110, filed July 8, 1987, now abandoned.

BACKGROUND OF THE INVENTION (a) Field of the Invention

This invention relates to novel 3-amino-1H-pyrazolo[3,4-b]quinolines and derivatives thereof, to methods for the preparation thereof, and compositions and methods for the use thereof as antiviral agents and/or vasodilating agents.

(b) Information Disclosure Statement (1) Prior Art

Prior art 3-amino-1H-pyrazolo[3,4-b]quinolines include the following:

3-amino-4-ethoxycarbonyl-1H-pyrazolo[3,4-b]quinoline, reported by Yoshida et al., Yakugaku Zasshi 96, 33–6 (1976); Chemical Abstracts 84:121754s.

3-Amino-4-carboxy-1-phenyl-1H-pyrazolo[3,4-b]quinoline, reported by Holla et al., Bull. Chem. Soc. Japan 57, 2984–6 (1984).

(2) Prior Disclosure

Neelima et al., J. Heterocyclic Chem. 23, 925 (1986) (actual publication date July 16, 1986) disclose a number of pyrazolo[3,4-b]quinoline derivatives including those represented by the following formulas

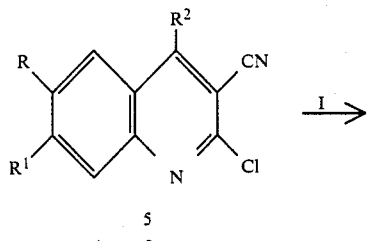

5
a: R = R$^1$ = R$^2$ = H
b: R = R$^1$ = OCH$_3$; R$^2$ = H
c: R = R$^1$ = H; R$^2$ = C$_2$H$_5$

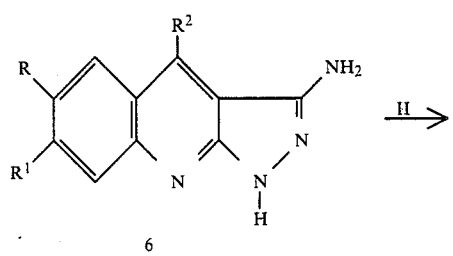

6
a: R = R$^1$ = R$^2$ = H
b: R = R$^1$ = OCH$_3$; R$^2$ = H
c: R = R = H; R = C$_6$H$_5$ [sic]

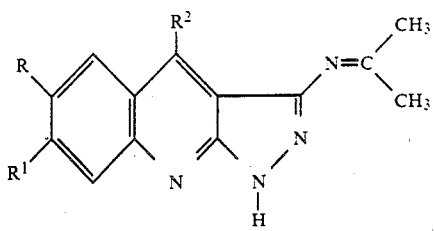

7
R = R$^1$ = H; R$^2$ = C$_6$H$_5$

Shown is the conversion of 2-chloro-3-quinolinecarbonitrile (5a) by reaction with hydrazine to produce 1H-pyrazolo[3,4-b]quinolin-3-amine (6a), and the corresponding reaction of 2-chloro-6,7-dimethoxy-3-quinolinecarbonitrile (5b) to produce 6,7-dimethoxy-1H-pyrazolo[3,4-b]quinolin-3-amine (6b). No utility is shown for compounds 6a and 6b. The Neelima et al. reference was published subsequent to completion of applicants' invention disclosed and claimed herein and in parent application Ser. No. 71,110 and less than one year prior to the filing date of application Ser. No. 71,110.

SUMMARY OF THE INVENTION

In a product aspect the invention relates to compounds of the formula

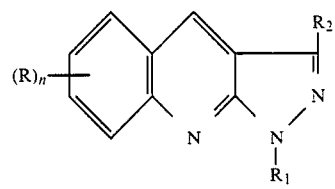

I wherein:

R is hydrogen or one or two substituents selected from hydroxy and lower-alkoxy;

R$_1$ is a member of the group consisting of hydrogen, lower-alkyl, phenyl, and —Y—R$_3$, wherein Y is lower-alkylene of 1–4 carbon atoms and R$_3$ is selected from the group consisting of lower-alkylamino, di(lower-alkyl)amino, 1-pyrrolidinyl, 1-piperidinyl, 4-morpholinyl, lower-alkoxycarbonyl, lower-alkylaminocarbonyl and di(lower-alkyl)aminocarbonyl;

R$_2$ is F, Cl, Br, CN, CONH$_2$, COOH, COO-lower-alkyl or (CH$_2$)$_m$NH$_2$ where m is 0 or 1;

and to pharmaceutically acceptable acid-addition salts thereof.

In a further product aspect, the invention relates to compositions for combating viruses which comprise an antivirally effective amount of a compound of Formula I in admixture with a suitable carrier or diluent.

In a process aspect, the invention relates to a process for preparing compounds of Formula I which comprises reacting a compound of the formula

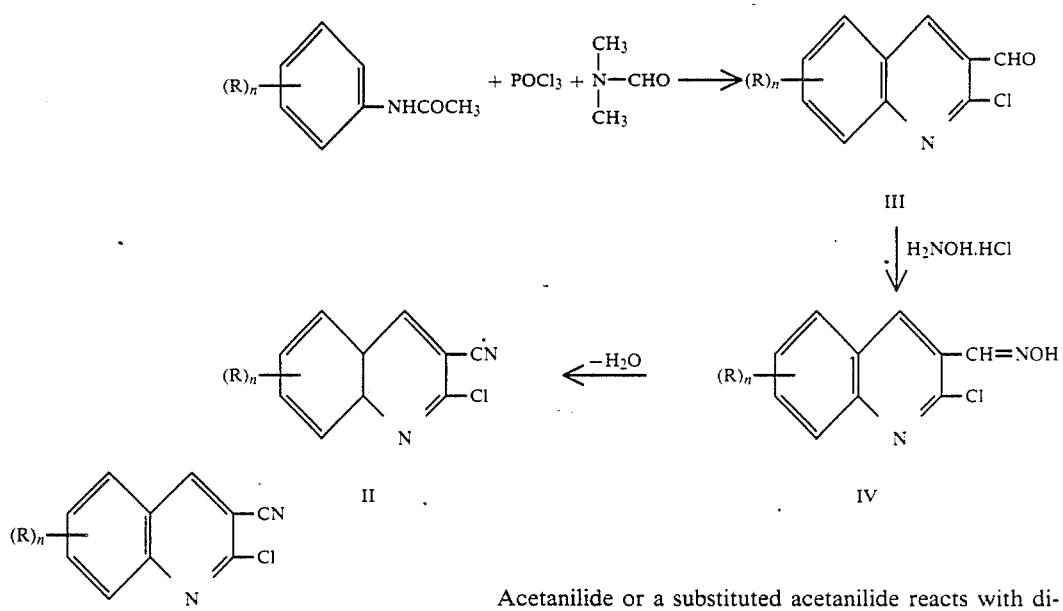

with hydrazine or a substituted hydrazine of the formula $H_2NNHR_1$.

In a further process aspect, the invention relates to a method for combating viruses which comprises contacting the locus of said viruses, including topical and systemic applications, with a composition containing an antivirally effective amount of a compound of Formula I.

DETAILED DESCRIPTION INCLUSIVE OF PREFERRED EMBODIMENTS

In the definitions of the variables in Formulas I and II above, the terms "lower-alkyl", "lower-alkoxy" and "lower-alkanoyl" stand for such groups preferably having from one to four carbon atoms. The term "halogen" stands for any of the four common halogen elements, fluorine, chlorine, bromine and iodine.

In the event that pharmaceutically acceptable acid-addition salts are prepared and used, the nature of the salt is immaterial provided it is derived from an acid the anion of Which is essentially innocuous to animal organisms. Examples of appropriate acid-addition salts include the hydrochloride, hydrobromide, sulfate, methanesulfonsate, maleate, citrate, tartrate, p-toluenesulfonate, cyclohexanesulfonate and the like.

In the preparation of the compounds of Formula I where $R_2$ is amino, the key reaction involving the formation of the pyrazolo[3,4-b]quinoline ring system comprises the reaction of a compound of Formula II with hydrazine or a substituted hydrazine $H_2NNHR_1$. The reaction takes place at a temperature of 50°–100° C. in an inert solvent, preferably a lower-alkanol such as methanol or ethanol, conveniently at the reflux temperature of the solvent. In the event a salt of the hydrazine is used, a buffer such as sodium acetate may be needed.

If compounds of Formula I where $R_1$ is phenyl or substituted phenyl are desired, the reaction with phenylhydrazine or substituted phenylhydrazine is preferably carried out in the presence of a strong base such as sodium hydride under anhydrous conditions at 0°–30° C.

The starting materials of Formula II are prepared according to the following flow-sheet:

Acetanilide or a substituted acetanilide reacts with dimethylformamide and phosphorus oxychloride to yield a 2-chloroquinolinecarboxaldehyde (III). The latter is converted to the corresponding oxime (IV) with hydroxylamine, and the oxime is dehydrated, e.g. with thionyl chloride or acetic anhydride, to yield the 2-chloroquinolinecarbonitrile (II). In this series of reactions R is preferably hydrogen or lower-alkoxy.

The compounds of Formula I where $R_1$ is other than hydrogen are alternatively prepared by alkylation of the compounds of Formula I where $R_1$ is H by reacting the latter with $R_1$-halide (halide being chloride, bromide or iodide) in the presence of a strong base under anhydrous conditions.

The compounds of Formula I where R is hydroxy are conveniently prepared by de-alkylation of the corresponding compounds of Formula I where R is lower-alkoxy. The de-alkylation is carried out by heating with hydrogen bromide or by heating with sodium hydride and butanethiol.

The compounds of Formula I where $R_2$ is Cl or Br are prepared from compounds of Formula I where $R_2$ is amino by a conventional diazotization reaction and conversion with cuprous chloride or cuprous bromide, respectively. A compound of Formula I where $R_2$ is Br may then be reacted with cuprous cyanide to form a compound of Formula I where $R_2$ is CN. The latter may then be reduced with lithium aluminum hydride to form a compound of Formula I where $R_2$ is aminomethyl ($CH_2NH_2$). In the event compounds of Formula I where $R_2$ is fluorine (F) are desired, they can be obtained by reacting the diazonium salt with fluoroboric acid.

The compounds of Formula I where $R_2$ is $CONH_2$ are prepared by mild hydrolysis of the compounds where R is CN. A convenient method is by heating the nitrile with water in the presence of an ion exchange resin. More vigorous hydrolysis of the nitrile in the presence of acid or base converts the nitrile to the corresponding carboxylic acid (R=COOH). Acid treatment of the nitrile in a lower-alkanol affords the corresponding ester (R=COO-lower-alkyl), which in turn can be hydrolyzed to the free acid (R=COOH).

The following examples will further illustrate the invention without the latter being limited thereby.

EXAMPLE 1

(a) 2-Chloro-6-methoxy-3-quinolinecarboxaldehyde

Phosphorus oxychloride (602 ml) was added dropwise over a period of 2.5 hours to 117 ml dimethylformamide stirred under nitrogen at 0° C. After the addition was complete, the mixture was stirred for 15 min longer and then 152.7 g 4-methoxyacetanilide was added. The reaction mixture was stirred for 15 min at 0° C. and then heated at reflux for 19 hours. The mixture was quenched in ice-water, and the resulting brown solid was extracted with boiling ethyl acetate. The product crystallized upon cooling to give 30.7 g 2-chloro-6-methoxy-3-quinolinecarboxaldehyde, m.p. 146°–147° C.

In another run starting with 215 ml phosphorus oxychloride, 84 ml dimethylformamide and 56 g 4-methoxyacetanilide, the 4-methoxyacetanilide was added portionwise to the $POCl_3—(CH_3)_2NCHO$ mixture at a temperature of 24°–50° C., and the reaction mixture was heated at 70° C. for about 16 hours. There was isolated from this mixture 35 g (46.6%) of 2-chloro-6-methoxy-3-quinolinecarboxaldehyde.

(b) 2-Chloro-6-methoxy-3-quinolinecarboxaldehyde oxime

A solution of 6.5 g hydroxylamine hydrochloride in 25 ml water was added to a suspension of 18.7 g 2-chloro-6-methoxy-3-quinolinecarboxaldehyde in 500 ml 95% ethanol. The mixture was stirred at room temperature for two hours and then heated at reflux for three hours. The reaction mixture was cooled to 0° C., filtered, and the filtrate concentrated to a volume of 200 ml. The product separated from solution to give 16.3 g 2-chloro-6-methoxy-3-quinolinecarboxaldehyde oxime, m.p. 195° C. (decompn.).

(c) 2-Chloro-6-methoxy-3-quinolinecarbonitrile

Thionyl chloride (7.9 ml) was added dropwise over a 12 min period to a stirred solution of 16.3 g 2-chloro-6-methoxy-3-quinolinecarboxaldehyde oxime in 160 ml dimethylformamide at 0° C. The reaction mixture was stirred for 15 min longer at 0° C. and then at room temperature overnight. The mixture was then quenched in ice-water, and the yellow solid product was collected, washed with water and dried in vacuo at 75° C. to give 14.8 g 2-chloro-6-methoxy-3-quinolinecarbonitrile, m.p. 201°–202° C.

(d) 6-Methoxy-1H-pyrazolo[3,4-b]quinolin-3-amine

To a stirred suspension of 14.7 g 2-chloro-6-methoxy-3-quinolinecarbonitrile in 465 ml absolute ethanol was added 17 ml of hydrazine hydrate. The mixture was stirred at reflux for 24 hours and then cooled to 0° C. The resulting solid product was collected by filtration and boiled with 200 ml water to remove any hydrazine dihydrochloride present. The resulting material was filtered and dried in vacuo (90° C.), and recrystallized from 300 ml dimethylformamide to give 12.3 g 6-methoxy-1H-pyrazolo[3,4-b]quinolin-3-amine as a bright-yellow solid, m.p. >300° C.

According to procedures analogous to those of Example 1 were prepared the following compounds of Examples 2–10:

EXAMPLE 2

(a) 2-Chloro-3-quinolinecarboxaldehyde, m.p. 148°–150° C. (from ethyl acetate).
(b) 2-Chloro-3-quinolinecarboxaldehyde oxime.
(c) 2-Chloro-3-quinolinecarbonitrile, m.p. 163°–164° C.
(d) 1H-Pyrazolo[3,4-b]quinolin-3-amine, orange solid, m.p. >300° C. (from ethanol).

EXAMPLE 3

(a) 2-Chloro-7-methoxy-3-quinolinecarboxaldehyde, m.p. 190°–193° C. (from dimethylformamide).
(b) 2-Chloro-7-methoxy-3-quinolinecarboxaldehyde oxime, tan powder, m.p. 195°–290° C. (decompn) (from methanol-ethyl acetate).
(c) 2-Chloro-7-methoxy-3-quinolinecarbonitrile, colorless powder, m.p. 199.5°–201.5° C. (from ethanol). In this instance the oxime dehydration reaction was carried out by heating in refluxing acetic anhydride.
(d) 7-Methoxy-1H-pyrazolo[3,4-b]quinolin-3-amine, golden crystals, m.p. 281°–283° C. (from ethanol).

EXAMPLE 4

(a) 2-Chloro-6,7-dimethoxy-3-quinolinecarboxaldehyde, m.p. 222°–224° C. (from ethyl acetate).
(b) 2-Chloro-6,7-dimethoxy-3-quinolinecarboxaldehyde oxime, m.p. 243° C. (decompn) (from ethanol).
(c) 2-Chloro-6,7-dimethyl-3-quinolinecarbonitrile, m.p. 233°–235° C.
(d) 6,7-Dimethoxy-1H-pyrazolo[3,4-b]quinolin-3-amine, bright orange-yellow powder, m.p. 269°–271° C.

EXAMPLE 5

(a) 2-Chloro-7-ethoxy-3-quinolinecarboxaldehyde, pale yellow solid, m.p. 165°–167° C. (from ethyl acetate).
(b) 2-Chloro-7-ethoxy-3-quinolinecarboxaldehyde oxime, m.p. 291°–298° C. (decompn) (from dimethylformamide).
(c) 2-Chloro-7-ethoxy-3-quinolinecarbonitrile, colorless solid, m.p. 165.5°–166.5° C. (from ethyl acetate).
(d) 7-Ethoxy-1H-pyrazolo[3,4-b]quinolin-3-amine, orange powder, m.p. 258°–259.5° C. (from ethanol).

EXAMPLE 6

(a) 2-Chloro-5-methoxy-3-quinolinecarboxaldehyde.
(b) 2-Chloro-5-methoxy-3-quinolinecarboxaldehyde oxime.
(c) 2-Chloro-5-methoxy-3-quinolinecarbonitrile.
(d) 5-Methoxy-1H-pyrazolo[3,4-b]quinolin-3-amine, yellow crystals, m.p. 280° C. (decompn).

EXAMPLE 7

7-Methoxy-1-methyl-1H-pyrazolo[3,4-b]quinolin-3-amine, orange solid, m.p. 201.5°–203° C. (from methanol), was prepared in 85% yield from 2-chloro-7-methoxy-3-quinolinecarbonitrile (Example 3c) and methylhydrazine in methanol.

EXAMPLE 8

6-Methoxy-1-methyl-1H-pyrazolo[3,4-b]quinolin-3-amine, orange crystals, m.p. 185°–186° C. (from ethanol) was prepared in 75% yield from 6-methoxy-3-quinolinecarbonitrile (Example 1c) and methylhydrazine in methanol.

EXAMPLE 9

7-Methoxy-1H-1-propylpyrazolo[3,4-b]quinolin-3-amine, orange-yellow powder, m.p. 156°–157° C., was prepared in 12% yield by heating 2-chloro-7-methoxy-3-quinolinecarbonitrile (Example 3c) with an excess of propylhydrazine oxalate in the presence of sodium acetate (in amount equivalent to the hydrazine) as a buffer in ethanol solution. The product was purified by chromatographic procedures.

EXAMPLE 10

1-Ethyl-7-methoxy-1H-pyrazolo[3,4-b]quinolin-3-amine, yellowish-orange solid, m.p. 230°–231° C., was prepared in 40% yield from 2-chloro-7-methoxy-3-quinolinecarbonitrile (Example 3c) and ethylhydrazine oxalate in the presence of sodium acetate. The product was purified by chromatographic procedures.

EXAMPLE 11

7-Methoxy-1-phenyl-1H-pyrazolo[3,4-b]quinolin-3-amine

To a suspension of 4.8 g sodium hydride (60%) in 200 ml dimethylformamide at 0° C. was added a solution of 9.9 ml phenylhydrazine in 250 ml dimethylformamide over a 15 min period. The mixture was stirred and allowed to warm to room temperature for 1 hour. 2-Chloro-7-methoxy-3-quinolinecarbonitrile (Example 3c) (19.68 g) was then added in portions. The reaction mixture was stirred overnight at room temperature, and then heated on a steam bath for two hours. Since starting material was still present, additional sodium hydride (3.2 g) was added and heating continued until thin layer chromatography indicated that no starting material remained. The mixture was quenched in saturated ammonium chloride solution and the mixture worked up in ethyl acetate solution. The crude product was purified by chromatography and recrystallized from ethyl acetate to give 2.3 g 7-methoxy-1-phenyl-1H-pyrazolo[3,4-b]quinolin-3-amine, brown solid, m.p. 159°–160° C.

EXAMPLE 12

3-Amino-1-methyl-1H-pyrazolo[3,4-b]quinolin-7-ol

A mixture of 20.9 g 7-methoxy-1-methyl-1H-pyrazolo[3,4-b]quinolin-3-amine (Example 7) and 420 ml 48% aqueous hydrobromic acid was stirred at reflux for 21 hours. The reaction mixture was quenched in ice-water and neutralized to pH 7.0 with ammonium hydroxide. The resulting yellow solid was collected by filtration, washed with water and recrystallized from 1100 ml absolute ethanol to provide 12.4 g (63%) 3-amino-1-methyl-1H-pyrazolo[3,4-b]quinolin-7-ol, orange-yellow solid, m.p. 288°–290° C. (decompn).

EXAMPLE 13

3-Amino-1H-pyrazolo[3,4-b]quinolin-7-ol, orange solid, m.p. >300° C. (from ethanol) was obtained by heating 7-methoxy-1H-pyrazolo[3,4-b]quinolin-3-amine (Example 3d) with hydrobromic acid in acetic acid solution. A sample of the compound was also obtained in the form of its hydrochloride salt, red solid, m.p. 192°–197° C. (decompn).

EXAMPLE 14

3-Amino-1H-pyrazolo[3,4-b]quinolin-6-ol, orange solid, m.p. >300° C. (from methyl ethyl ketone and from methanol) was obtained from 6-methoxy-1H-pyrazolo[3,4-b]quinolin-3-amine (Example 1d) according to the procedure of Example 12.

EXAMPLE 15

7-Methoxy-1-[2-(4-morpholinyl)ethyl]-1H-pyrazolo[3,4-b]quinolin-3-amine

A mixture of 17.1 g 7-methoxy-1H-pyrazolo[3,4-b]quinolin-3-amine (Example 3d), 15.25 g 4-(2-chloroethyl)morpholine hydrochloride, 7.2 g sodium hydride and 500 ml dimethylformamide was stirred at room temperature for about 16 hours. The solvent was then removed by evaporation, and the residue dissolved in 1N hydrochloric acid and extracted with ethyl acetate. The aqueous layer was made basic with carbonate to pH 8 and extracted with chloroform. The chloroform extracts were washed with water, dried over magnesium sulfate and passed through a silica gel pad. The pad was eluted with warm ethyl acetate, the product isolated and recrystallized from ethyl acetate to give 9.2 g 7-methoxy-1-[2-(4-morpholinyl)ethyl]-1H-pyrazolo[3,4-b]quinolin-3-amine, orange solid, m.p. 166°–168° C.

By replacing the 4-(2-chloroethyl)morpholine hydrochloride in the foregoing procedure by a molar equivalent amount of 1-(2-chloroethyl)pyrrolidine or 1-(2-chloroethyl)piperidine, it is contemplated that there can be obtained 7-methoxy-1-[2-(1-pyrrolidinyl)ethyl]-1H-pyrazolo[3,4-b]quinolin-3-amine or 7-methoxy-1-[2-(1-piperidinyl)ethyl]-1H-pyrazolo[3,4-b]quinolin-3-amine.

The following Examples 16–22 were carried out by alkylation procedures similar to that of Example 15. In some instances, minor amounts of additional solvents such as dimethylsulfoxide or tetrahydrofuran were added to the dimethylformamide reaction medium.

EXAMPLE 16

1-[2-(Diethylamino)ethyl]-6-methoxy-1H-pyrazolo[3,4-b]quinolin-3-amine, bright-yellow solid, m.p. 143°–145° C., was prepared from 6-methoxy-1H-pyrazolo[3,4-b]quinolin-3-amine (Example 1d) and 2-(diethylamino)ethyl chloride hydrochloride.

EXAMPLE 17

1-[3-(Dimethylamino)propyl]-6-methoxy-1H-pyrazolo[3,4-b]quinolin-3-amine, orange solid, m.p. 152°–153° C. (from ethyl acetate), was prepared from 6-methoxy-1H-pyrazolo[3,4-b]quinolin-3-amine (Example 1d) and 3-(dimethylamino)propyl chloride hydrochloride.

EXAMPLE 18

1-[2-(Dimethylamino)ethyl]-7-methoxy-1H-pyrazolo[3,4-b]quinolin-3-amine, orange-yellow needles, m.p. 139°–140° C., was prepared from 7-methoxy-1H-pyrazolo[3,4-b]quinolin-3-amine (Example 3d) and 2-(dimethylamino)ethyl chloride hydrochloride.

EXAMPLE 19

Ethyl 3-amino-7-methoxy-1H-pyrazolo[3,4-b]quinolin-1-acetate, bright-yellow solid, m.p. 192°–193° C. (from isopropyl alcohol), was prepared from 7- methoxy-1H-pyrazolo[3,4-b]quinolin-3-amine (Example 3d) and ethyl bromoacetate.

EXAMPLE 20

Ethyl 3-amino-6-methoxy-1H-pyrazolo[3,4-b]quinolin-1-acetate, bright-yellow solid, m.p. 198°–199° C. (from ethanol), was prepared from 6-methoxy-1H-pyrazolo[3,4-b]quinolin-3-amine (Example 1d) and ethyl bromoacetate.

EXAMPLE 21

1-[2-(Dimethylamino)ethyl]-6-methoxy-1H-pyrazolo[3,4-b]quinolin-3-amine, orange solid, m.p. 160°–162° C. (from ethyl acetate/hexane), was prepared from 6-methoxy-1H-pyrazolo[3,4-b]quinolin-3-amine (Example 1d) and 2-(diethylamino)ethyl chloride.

EXAMPLE 22

1-[2-(Diethylamino)ethyl]-7-methoxy-1H-pyrazolo[3,4-b]quinolin-3-amine, bright-yellow solid, m.p. 96°–98° C. (from ethyl acetate), was prepared from 7-methoxy-1H-pyrazolo[3,4-b]quinolin-3-amine (Example 3d) and 2-(diethylamino)ethyl chloride.

EXAMPLE 23

3-Amino-1-[2-(diethylamino)ethyl]-7-methoxy-1H-pyrazolo[3,4-b]quinolin-7-ol

Butanethiol (5.34 ml) was added to a mixture of 13.0 g 1-[2-(diethylamino)ethyl]-7-methoxy-1H-pyrazolo[3,4-b]quinolin-3-amine (Example 22) and 2.0 g sodium hydride in 150 ml dimethylformamide, and the reaction mixture was heated at reflux for about 16 hours. The resulting mixture was treated with 2N hydrochloric acid to pH 7-8, the volatile materials removed by distillation and evaporation, and the residue acidified with 2N hydrochloric acid and extracted with ethyl acetate. The aqueous layer was made strongly basic, extracted to remove starting material, and finally adjusted to PH 8 to obtain the desired product. There was obtained 2.5 g of 3-amino-1-[2-(diethylamino)ethyl]-7-methoxy-1H-pyrazolo[3,4-b]quinolin-7-ol, orange solid, m.p. 232°–235° C.

EXAMPLE 24

3-Amino-1-[2-(dimethylamino)ethyl]-1H-pyrazolo[3,4-b]quinolin-7-ol, orange solid, m.p. 235°–238° C. (from ethyl acetate), was prepared from 1-[2-(diemthylamino)ethyl]-7-methoxy-1H-pyrazolo[3,4-b]quinolin-3-amine (Example 18), sodium hydride and butanethiol according to the procedure of Example 23.

EXAMPLE 25

3-Amino-6-methoxy-N,N-dimethyl-1H-pyrazolo[3,4-b]quinolin-1-acetamide

To a saturated solution of dimethylamine in 250 ml methanol at 0° C. was added 4.5 g ethyl 3-amino-6-methoxy-1H-pyrazolo[3,4-b]quinolin-1-acetate (Example 20), and the mixture was stirred at 0° C. for one hour, at room temperature for 48 hours and at reflux for two hours. The reaction mixture was cooled to room temperature and the solid product was collected by filtration and chromatographed on silica gel using 95% chloroform/2.5% isopropyl alcohol/2.5% isopropylamine amine as eluant. The appropriate fractions were combined and evaporated to give 2.0 g 3-amino-6-methoxy-N,N-dimethyl-1H-pyrazolo[3,4-b]quinolin-1-acetamide, orange solid, m.p. 251°–253° C.

EXAMPLE 26

3-Amino-6-methoxy-N-methyl-1H-pyrazolo[3,4-b]quinolin-1-acetamide, orange solid, m.p. 255°–258° C. (from chloroform), was prepared according to the procedure of Example 25 but replacing the dimethylamine by methylamine.

EXAMPLE 27

1-[2-(Methylamino)ethyl]-6-methoxy-1H-pyrazolo[3,4-b]quinolin-3-amine

To a suspension of 2.00 lithium aluminum hydride in 100 ml tetrahydrofuran was added, portionwise, 5.5 g 3-amino-6-methoxy-N-methyl-1H-pyrazolo[3,4-b]quinolin-1-acetamide (Example 26) and 50 ml of tetrahydrofuran. The mixture was heated at reflux for 4 hours, then cooled and poured into ice-water. The solid product was collected and chromatographed on silica gel using 95% chloroform/5% isopropylamine as eluant. The fractions were combined and evaporated, and the product recrystallized from ether/hexane to give 0.77 g 1-[2-(methylamino)ethyl]-6-methoxy-1H-pyrazolo[3,4-b]quinolin-3-amine, orange solid, m.p. 142°–144° C.

EXAMPLE 28

3-Amino-7-methoxy-N-ethyl-1H-pyrazolo[3,4-b]quinolin-1-acetamide, bright-yellow solid, m.p. 237°–239° C. (from methanol), was prepared according to the procedure of Example 25 but replacing the dimethylamine by ethylamine.

EXAMPLE 29

1-[2-(Ethylamino)ethyl]-7-methoxy-1H-pyrazolo[3,4-b]quinolin-3-amine, orange solid, m.p. 110°–111° C. (from ethyl acetate), was prepared from 3-amino-7-methoxy-N-ethyl-1H-pyrazolo[3,4-b]quinolin-1-acetamide (Example 28) and lithium aluminum hydride according to the procedure of Example 27.

EXAMPLE 30

1-[(Dimethylamino)methyl]-7-methoxy-1H-pyrazolo[3,4-b]quinolin-3-amine

To a solution of 15 g 7-methoxy-1H-pyrazolo[3,4-b]quinolin-3-amine (Example 3d) in 190 ml ethanol was added 16 ml 47% aqueous dimethylamine and 6.5 ml 37% aqueous formaldehyde. The reaction mixture was stirred at room temperature overnight, then concentrated by evaporation, and the residue was recrystallized from ethanol to give 10.8 g 1-[(dimethylamino)methyl]-7-methoxy-1H-pyrazolo[3,4-b]quinolin-3-amine, bright-yellow solid, m.p. 156°–158° C.

EXAMPLE 31

3-Chloro-6-methoxy-1-methyl-1H-pyrazolo[3,4-b]quinoline

6-Methoxy-1-methyl-1H-pyrazolo[3,4-b]quinolin-3-amine (Example 8) (16.0 g) was dissolved in a cooled mixture of 40 ml concentrated sulfuric acid and 40 ml water. To this was added 6.9 g sodium nitrite in 20 ml water at a rate of 1 drop per second at 10° C. After 5 min the reaction mixture was poured into a solution of 19.8 g cuprous chloride in 100 ml concentrated hydrochloric acid and 200 ml water, and then slowly heated to 70° C. The reaction mixture was then cooled, ammonium hydroxide and 1.0 g sodium cyanide was added, solids removed by filtration and the filtrate extracted with ethyl acetate. From the extracts was isolated 12 g of solid which was chromatographed and recrystallized to give 3.5 g 3-chloro-6-methoxy-1-methyl-1H-pyrazolo[3,4-b]quinoline, yellow solid, m.p. 138°–139° C.

By replacing the cuprous chloride solution in the foregoing preparation by a solution of fluoroboric acid, it is contemplated that there can be obtained 3-fluoro-6-methoxy-1-methyl-1H-pyrazolo[3,4-b]quinoline.

EXAMPLE 32

3-Bromo-6-methoxy-1-methyl-1H-pyrazolo[3,4-b]quinoline, yellow solid, m.p. 145°–146° C., was prepared according to the procedure of Example 31 but replacing the cuprous chloride solution by a solution of cuprous bromide in water containing a trace of sodium cyanide.

EXAMPLE 33

6-Methoxy-1-methyl-1H-pyrazolo[3,4-b]quinoline-3-carbonitrile

A mixture of 32.0 g 3-bromo-6-methoxy-1-methyl-1H-pyrazolo[3,4-b]quinoline (Example 32) and 20.2 g cuprous bromide in 220 ml N-methylpyrrolidine was stirred and heated at reflux for 3 hours. The reaction mixture was poured into ice-water, and the solid product was collected by filtration. The latter product was treated with dilute aqueous sodium cyanide and purified by extraction with ethyl acetate and chromatography to give 4.5 g 6-methoxy-1-methyl-1H-pyrazolo[3,4-b]quinoline-3-carbonitrile, bright-yellow solid, m.p. 190°–191° C., when recrystallized from methanol.

EXAMPLE 34

7-Methoxy-1-methyl-1H-pyrazolo[3,4-b]quinoline-3-methanamine

A mixture of 8.6 g 6-methoxy-1-methyl-1H-pyrazolo[3,4-b]quinoline-3-carbonitrile (Example 33) and 3.8 g lithium aluminum hydride in 500 ml tetrahydrofuran was stirred at room temperature for about sixteen hours. The crude product was isolated and dissolved in 200 ml toluene. Ethanol (10 ml) and 2 g palladium-on-carbon catalyst (10%) was added, and the mixture was heated to reflux and stirred for about sixteen hours. The reaction mixture was filtered and concentrated, and the residue was chromatographed and crystallized from ethanol to give 2.9 g 7-methoxy-1-methyl-1H-pyrazolo[3,4-b]quinoline-3-methanamine, brownish-yellow solid, m.p. 119°–120° C.

EXAMPLE 35

6-Methoxy-1-methyl-1H-pyrazolo[3,4-b]quinoline-3-carboxamide

A mixture of 6.20 g 6-methoxy-1-methyl-1H-pyrazolo[3,4-b]quinoline-3-carbonitrile (Example 33), 250 ml water and 13.5 ion exchange resin (Amberlite IRA-100, OH$^-$ form) was stirred and heated at reflux until hydrolysis was complete. The product was isolated and recrystallized from ethyl acetate-hexane to give 2.7 g 6-methoxy-1-methyl-1H-pyrazolo[3,4-b]quinoline-3-carboxamide, yellow solid, m.p. 268°–270° C.

EXAMPLE 36

3-Bromo-1-[2-(dimethylamino)ethyl]-6-methoxy-1H-pyrazolo[3,4-b]quinoline, yellow solid, m.p. 85°–87° C., was prepared from 1-[2-(dimethylamino)ethyl]-6-methoxy-1H-pyrazolo[3,4-b]quinolin-3-amine (Example 21) via its diazonium salt and cuprous bromide.

EXAMPLE 37

3-Bromo-1-[2-(dimethylamino)ethyl]-7-methoxy-1H-pyrazolo[3,4-b]quinoline, yellow solid, m.p. 106°–107° C., was prepared from 1-[2-(dimethylamino)ethyl]-7-methoxy-1H-pyrazolo[3,4-b]quinolin-3-amine (Example 18) via its diazonium salt and cuprous bromide.

EXAMPLE 38

,1[2-(Dimethylamino)ethyl]-7-methoxy-1H-pyrazolo[3,4-b]quinoline-3-carbonitrile, pale yellow solid, m.p. 146°–147° C., was prepared from 3-bromo-1-[2-(dimethylamino)ethyl]-7-methoxy-1H-pyrazolo[3,4-b]quinoline (Example 37) and cuprous cyanide in dimethylformamide solution, heated at reflux under nitrogen for about sixteen hours.

EXAMPLE 39

Methyl 1-[2-(dimethylamino)ethyl]-7-methoxy-1H-pyrazolo[3,4-b]quinoline-3-carboxylate A sample of 1-[2-(dimethylamino)ethyl]-7-methoxy-1H-pyrazolo[3,4-b]quinoline-3-carbonitrile (Example 38) (about 1 g) was added to 30 ml methanol saturated with hydrogen chloride, and the mixture was heated at reflux for about 16 hours. The reaction mixture was concentrated, dilute aqueous potassium carbonate added to the residue, and the product extracted with methylene dichloride. The extracts were dried (MgSO$_4$) and concentrated, and the residue chromatographed on silica (50/50 ethanol/ethyl acetate) to give 500 mg methyl 1-[2-(dimethylamino)ethyl]-7-methoxy-1H-pyrazolo[3,4-b]quinoline-3-carboxylate, pale yellow powder, m.p. 127°–128° C.

Methyl 1-[2-(dimethylamino)ethyl]-7-methoxy-1H-pyrazolo[3,4-b]quinoline-3-carboxylate can be hydrolyzed by heating it with aqueous potassium carbonate to produce the corresponding acid, 1-[2-(dimethylamino)ethyl]-7-methoxy-1H-pyrazolo[3,4-b]quinoline-3-carboxylic acid.

EXAMPLE 40

3-Chloro-1-(2-dimethylaminoethyl)-7-methoxy-1H-pyrazolo[3,4-b]quinoline was prepared by diazotization of 1-(2-dimethylaminoethyl)-7-methoxy-1H-pyrazolo[3,4-b]quinolin-3-amine (Example 18) and reaction of the diazonium salt with cuprous chloride. The product was obtained in 40% yield in the form of a pale yellow powder, m.p. 86°–88° C. when recrystallized from ether/hexane.

EXAMPLE 41

3-Bromo-7-methoxy-1-(2-methylaminoethyl)-1H-pyrazolo[3,4-b]quinoline was prepared by demethylation of 3-bromo-1-[2-(dimethylamino)ethyl]-7-methoxy-1H-pyrazolo[3,4-b]quinoline (Example 37) by the method of J. Org. Chem. 49, 2081 (1984), as follows: to a mixture of 15 g of the compound of Example 37 and 150 ml methylene dichloride at 0° C. was added dropwise a solution of 6.7 g α-chloroethyl chloroformate in 30 ml methylene dichloride. The reaction mixture was heated at reflux for one hour and then concentrated to remove solvent. The residue in 300 ml methanol was heated at reflux for one hour. The methanol was removed, ice-water and concentrated ammonium hydroxide added to the residue, and the product collected and recrystallized from ethyl acetate to give 7.12 g 3-bromo-7-methoxy-1-(2-methylaminoethyl)-1H-pyrazolo[3,4-b]quinoline, light yellow powder, m.p. 100°–101° C.

EXAMPLE 42

3-Chloro-7-methoxy-1H-pyrazolo[3,4-b]quinoline was prepared from 7-methoxy-1H-pyrazolo[3,4-b]quinolin-3-amine (Example 3d) by diazotization in hydrochloric acid. The product was recrystallized from ethanol and then from acetic acid and obtained in about 25% yield as a brown solid, m.p. 296°–297° C.

EXAMPLE 43

3-Bromo-1-isopropyl-7-methoxy-1H-pyrazolo[3,4-b]quinoline was prepared from 1-isopropyl-7-methoxy-1H-pyrazolo[3,4-b]quinolin-3-amine by preparation of the diazonium salt in hydrobromic acid followed by reaction with cuprous bromide. The product was recrystallized from ether/hexane and obtained in the form of a brown solid, m.p. 130°–131° C.

The intermediate 1-isopropyl-7-methoxy-1H-pyrazolo[3,4-b]quinolin-3-amine was prepared by alkylation of 7-methoxy-1H-pyrazolo[3,4-b]quinolin-3-amine (Example 3d) with 2-iodopropane in the presence of sodium hydride.

EXAMPLE 44

The reaction of 7-methoxy-1H-pyrazolo[3,4-b]quinolin-3-amine (Example 3d) and (2-mesyloxypropyl)dimethylamine in the presence of sodium hydride in dimethylformamide by a procedure analogous to that of Example 15 afforded a mixture of products, the major product being (a) 1-[2-(dimethylamino)-2-methylethyl]-7-methoxy-1H-pyrazolo[3,4-b]quinolin-3-amine, orange solid, m.p. 165°–166° C. when recrystallized from ethyl acetate; and the minor product being (b) 1-[2-(dimethylamino)-1-methylethyl]-7-methoxy-1H-pyrazolo[3,4-b]quinolin-3-amine, orange powder, m.p. 154°–157° C. when recrystallized from ethyl acetate. The major product was obtained in 62% yield by simple fractional crystallization. The minor product was obtained in 16% yield from the mother liquors by chromatography on silica and elution with 3% isopropyl acetate in chloroform.

EXAMPLE 45

3-Chloro-1-[2-(dimethylamino)-2-methylethyl]-7-methoxy-1H-pyrazolo[3,4-b]quinoline, pale yellow solid, m.p. 78°–79° C. (from ether/hexane) was prepared by diazotization of 1-[2-(dimethylamino)-2-methylethyl]-7-methoxy-1H-pyrazolo[3,4-b]quinolin-3-amine (Example 44a) and treatment of the diazonium salt with cuprous chloride.

EXAMPLE 46

3-Chloro-1-[2-(methylamino)-2-methylethyl]-7-methoxy-1H-pyrazolo[3,4-b]quinoline was prepared by demethylation of 3-chloro-1-[2-(dimethylamino)-2-methylethyl]-7-methoxy-1H-pyrazolo[3,4-b]quinoline (Example 45), with α-chloroethyl chloroformate according to the procedure of Example 41, and was obtained in the form of a colorless solid, m.p. 98°–100° C.

The activity of the compounds of the invention against herpes simplex virus type 2 (HSV-2) was determined by measuring plaque-reduction activity on mouse embryo fibroblast monolayers. Two-day-old monolayers of Balb/c or ICR mouse embryo fibroblasts (MEF) were infected with approximately 80 pfu (plaque forming units) of HSV-2 (Curtis strain) in the presence of various concentrations of the test compounds. After a 1 hour absorption period at 37° C. and 2% $CO_2$, the inoculum was removed and an overlay containing equal parts of 2X MS medium supplemented with 10% fetal calf serum (FSC) and 1% molten Seakem agarose was added to cell monolayers. Both the inocula and the overlay mixtures contained 1:200 dilutions of the test compound made from stock dilutions in dimethylsulfoxide. After incubation at 37° C. and 2% $CO_2$ for 2 days, the monolayers were fixed with 5% glutaraldehyde and stained with 0.25% aqueous crystal violet. The plaques were quantitated by visual inspection. The minimum inhibitory concentration (MIC) for a compound was defined as the concentration in micrograms per milliliter (μg/ml) which inhibited the number of plaques by 50%. The MIC was calculated by interpolation.

The result of the testing for the compounds of the indicated Examples are given in the following table.

| Example | MIC (MTL) (μg/ml) |
| --- | --- |
| 1(d) | 1.5 (12.5) |
| 2(d) | NA (25) |
| 3(d) | 4.3 (12.5) |
| 4(d) | NA (12.5) |
| 5(d) | 17 (25) |
| 6(d) | 13 (25) |
| 7 | 6.4 (12.5) |
| 8 | NA (12.5) |
| 9 | 5.3 (10) |
| 10 | 7.8 (12.5) |
| 11 | 19 (25) |
| 12 | NA (>12.5) |
| 13 | 13 (25) |
| 14 | NA (3.1) |
| 15 | 44 (50) |
| 16 | NA (>100) |
| 17 | 78 (>100) |
| 18 | 12 (25) |
| 19 | 12 (25) |
| 20 | NA (50) |
| 21 | 24 (50) |
| 22 | 23 (50) |
| 23 | 39 (50) |
| 24 | 13 (>25) |
| 25 | NA (>100) |
| 26 | NA (>100) |
| 27 | 13 (25) |
| 28 | NA (25) |
| 29 | 6.7 (25) |
| 30 | 2.6 (25) |
| 31 | 18 (50) |
| 32 | NA (12.5) |
| 33 | 42 (>100) |
| 34 | 15 (25) |
| 35 | 7 (12.5) |
| 36 | 4.3 (25) |
| 37 | 0.97 (3.1) |
| 38 | 0.82 (12.5) |
| 39 | 2.3 (3.1) |
| 40 | 0.67 (>3.1) |
| 41 | 0.72 (6.2) |
| 42 | NA (>12.5) |
| 43 | NA (>12.5) |
| 44a | 11 (>12.5) |
| 44b | NA (>12.5) |
| 45 | 0.88 (1.6) |

-continued

| Example | MIC (MTL) (μg/ml) |
|---|---|
| 46 | 3.7 (>12.5) |

NA = Not active below maximum testable level (MTL).

The antiviral compounds are formulated for use by preparing a dilute solution or suspension of an antivirally effective amount in a pharmaceutically acceptable aqueous, organic or aqueous-organic medium for topical or parenteral administration, or are prepared in tablet, capsule, or acueous suspension form with conventional excipients for oral administration.

Certain of the compounds of the invention were found to have vasodilator activity when tested in a phenylephrine-contracted aortic ring preparation from the spontaneously hypertensive rat (SHR), as follows. Aortic ring preparations from SHR are suspended in buffered physiological saline and induced to contract by addition of 1 μM phenylephrine, a selective $\alpha_1$-adrenergic agonist. When a sustained contraction is obtained, the test compound is added cumulatively in ascending concentrations beginning at 1 μM. At the end of the addition of the test compound, a 200 μM concentration of papaverine is added to the organ bath for induction of a 100% vasodilator response. Percent relaxation by the test compound is expressed as a percent of maximal relaxation induced by papaverine. Where possible, the activity of the test compound is calculated as an $EC_{50}$, which is defined as the concentration of vasodilator that causes 50% of the maximally induced relaxation caused by papaverine. By this procedure, $EC_{50}$ values for certain compounds of the invention were determined with the following results:

| Example | $EC_{50}$ (μM) |
|---|---|
| 1(d) | 31 |
| 2(d) | 26 |
| 3(d) | 21 |
| 4(d) | 18 |
| 7 | 43 |
| 12 | 57 |
| 13 | 87 |
| 14 | 25 |
| 16 | 40 |
| 17 | 91 |
| 18 | 25 |
| 19 | 71 |
| 21 | 38 |
| 22 | 22 |
| 23 | 33 |
| 25 | 116 |
| 28 | 70 |
| 35 | 9 |

The compounds having vasodilator activity are formulated for use by preparing a dilute solution or suspension of a vasodilatorily effective amount in a pharmaceutically acceptable aqueous, organic or aqueous-organic medium for parenteral administration, or are prepared in tablet, capsule, or aqueous suspension form with conventional excipients for oral administration.

We claim:

1. A compound of the formula

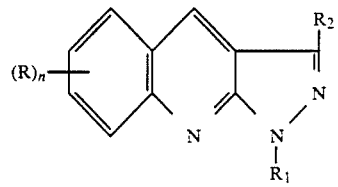

wherein:

R is hydrogen or one or two substituents selected from hydroxy and lower-alkoxy wherein n is 1 or 2;

$R_1$ is a member of the group consisting of hydrogen, lower-alkyl, phenyl, and —Y—$R_3$, wherein Y is lower-alkylene of 1–4 carbon atoms and $R_3$ is selected from the group consisting of lower-alkylamino, di(lower-alkyl)amino, 1-pyrrolidinyl, 1-piperidinyl, 4-morpholinyl, lower-alkoxycarbonyl, lower-alkylaminocarbonyl and di(lower-alkyl)aminocarbonyl;

$R_2$ is F, Cl, Br, CN, $CONH_2$ COOH, COO-lower-alkyl or $(CH_2)_m NH_2$ where m is 0 or 1;

or a pharmaceutically acceptable acid-addition salt thereof.

2. A compound according to claim 1 wherein $R_1$ is hydrogen and $R_2$ is amino.

3. 7-Methoxy-1H-pyrazolo(3,4-b)quinolin-3-amine, according to claim 2.

4. 6-Methoxy-1H-pyrazolo(3,4-b)quinolin-3-amine, according to claim 2.

5. 1H-Pyrazolo(3,4-b)quinolin-3-amine, according to claim 2.

6. 6,7-Dimethoxy-1H-pyrazolo(3,4-b)quinolin-3-amine, according to claim 2.

7. A compound according to claim 1 where $R_2$ is Cl.

8. 3-Chloro-1-(2-(methylamino)-2-methylethyl)-7-methoxy-1H-pyrazolo(3,4-b)quinoline, according to claim 7.

9. A composition for combating viruses which comprises an antivirally effective amount of a compound according to claim 1, in admixture with a suitable carrier or diluent.

10. A composition according to claim 9 for combating herpesviruses.

11. A method for combating viruses which comprises contacting the locus of said viruses, including topical and systemic applications, with a composition according to claim 9.

12. A method according to claim 11 for combating herpesviruses.

* * * * *